United States Patent
Han et al.

(10) Patent No.: US 9,138,581 B2
(45) Date of Patent: Sep. 22, 2015

(54) METHOD FOR THE TREATMENT OF AUTISM

(76) Inventors: Jisheng Han, Beijing (CN); Rong Zhang, Beijing (CN); Songping Han, Beijing (CN); Meixiang Jia, Beijing (CN); Jishui Zhang, Beijing (CN); Xiuting Zhang, Zhouozhou (CN)

( * ) Notice: Subject to any disclaimer, the term of this patent is extended or adjusted under 35 U.S.C. 154(b) by 18 days.

(21) Appl. No.: 13/821,221
(22) PCT Filed: Sep. 6, 2011
(86) PCT No.: PCT/CN2011/001508
§ 371 (c)(1),
(2), (4) Date: Sep. 20, 2013
(87) PCT Pub. No.: WO2012/031456
PCT Pub. Date: Mar. 15, 2012

(65) Prior Publication Data
US 2014/0303683 A1    Oct. 9, 2014

(30) Foreign Application Priority Data
Sep. 6, 2010    (CN) .......................... 2010 1 0272992

(51) Int. Cl.
*A61N 1/18*    (2006.01)
*A61N 1/36*    (2006.01)
*A61H 39/00*    (2006.01)

(52) U.S. Cl.
CPC .......... *A61N 1/36025* (2013.01); *A61H 39/002* (2013.01); *A61N 1/36014* (2013.01)

(58) Field of Classification Search
None
See application file for complete search history.

(56) References Cited

PUBLICATIONS

Lu W, Acupuncture for Autism: A promising therapy; Aug. 18, 2013. Lecture Slides Harvard Medical School, Dana-Farber Cancer Institute.*

* cited by examiner

*Primary Examiner* — Brian T Gedeon
(74) *Attorney, Agent, or Firm* — Ladas & Parry, LLP

(57) ABSTRACT

The present invention provides a method for treating autism. The method comprises following steps: step 1, applying a first electrical current stimulation of 30 minutes in the vicinity of the Hegu acupuncture point and the Nei guan acupuncture point at one side of the patient, wherein the first electrical current stimulation has a first slow-quick waveform, and the maximum current of the first electrical current stimulation is 3-10 mA; and step 2, applying a second electrical current stimulation of 30 minutes in the vicinity of the Zusanli acupuncture point, and the Sanyinjiao acupuncture point at opposite side of the patient, wherein the second electrical current stimulation has a second slow-quick waveform, and the maximum current of the second electrical current stimulation is 4-15 mA. The above-mentioned method may actually aim at the etiology in the biological and medical aspects, and results in actual therapeutic significance. In the course of treatment, the above-mentioned method is not found to have any side effects, so it can be used for a long time. The present method of the present application is non-invasive and painless, and it is acceptable for children, and suitable for family use. The method can obviously improve the symptoms of autism. The clinical manifestations is an increase of passive and active language, an improvement of social interaction-ability, emotion becoming stable, a better sleep (sleep quickly, a long time). In addition, the method is simple and do not need an acupuncturist.

14 Claims, 5 Drawing Sheets

Hegu acupuncture point

Hegu
acupuncture point

METHOD FOR THE TREATMENT OF AUTISM

CROSS-REFERENCE TO RELATED APPLICATIONS

This application is the U.S. National Stage of International Patent Application No. PCT/CN2011/001508 filed on Sep. 6, 2011, which claims priority from Chinese Patent Application No. 201010272992.5 filed on Sep. 6, 2010, the disclosures of which are hereby incorporated by reference in their entireties.

FIELD OF THE INVENTION

The present invention relates to a method for the treatment of Autism.

DESCRIPTION OF THE RELATED ART

Autism is a mental development disorder relating to young children, its main characteristics include obstacles to social communication, communication disorders, narrow interests, stiff and repetitive behavior.

At present, the methods for treating autism mainly including behavior modification therapy and drug treatment. Behavior modification therapy requires individualized, systemic, strict, consistent and scientific behavior modification. For getting a better treatment effect, the behavior modification must be executed at a high frequency. For example, 20 to 40 hours every week, 1 to 3 times a day, 3 hours each time, and completing the behavior modification tasks within the 3 hours. This should be implemented in particular training institutions which relates to a high investment and a high treatment costs for the patients. For example, the treatment cost for Chinese children with autism is usually 3000 to 5000 Chinese Yuan per month, in US, the cost is as high as $9000 a month. In addition, this method is a method of pedagogy, but autism is a kind of disease, and relates to biological changes in the brain of a patient. Training can only provide external stimuli, rather than changing the patient's physical condition.

With respect to drugs, there is not a specific drug for the autism treatment. Risperdal (risperidone, an antipsychotic drug) has been approved by the United States Food and Drug Administration (FDA) to improve the problem regarding rage, attack, self-injury, sleep of children with autism. But the drug has no obvious effect for improving the abilities of language and communication of children with autism. In addition, if taking risperidone for a long-term, patients will be apathetic, no interest for anything, and even other side effects.

In 2006, Hollander, E use oxytocin in autism treatment, and apply for a patent. Hollander, E found that intravenous oxytocin can improve the language ability of patients, reduce the rigid motion, and the function may be sustainable for 2 weeks. However, Oxytocin has not yet been approved as a treatment for autism means. In addition, this medicine is exogenous, its side effect is unknown.

SUMMARY OF THE INVENTION

Acupuncture is an important part of traditional Chinese medicine, we and other laboratories found that a stimulation of 2 Hz electro-acupuncture can increase the release of 5-HT in the brain, and a stimulation of 15 Hz can increase OXT and AVP content in the brain, therefore, we speculate that acupuncture can affect the symptoms of autistic children by changing the neurotransmitters in the brain.

Autism etiology is complex, involving genetics, developmental biology and environmental science etc. It is found that that the abnormal incidence of some neurotransmitters may be linked to autism, such as (1) serotonin (5-HT); abnormal and reduce of metabolism; (2) decreasing of oxytocin (Oxytocin, OXT) levels in plasma of children, it is found that intravenous injection of OXT into the autistic volunteers may reduce stereotypic behavior of patients, and improve the ability of language analysis and apperceiving. Hollander, E applied for a patent of the usage of oxytocin in autism treatment; (3) vasopressin (Arginine vasopressin, AVP) has the similar structure and function with OXT.

According to one aspect of the present invention, a method for the treatment of Autism comprises following steps: step 1, applying a first electrical current stimulation of 30 minutes in the vicinity of the Hegu acupuncture point and the Nei guan acupuncture point at one side of the patient, wherein the first electrical current stimulation has a first slow-quick waveform, and the maximum current of the first electrical current stimulation is 3-10 mA; and step 2, applying a second electrical current stimulation of 30 minutes in the vicinity of the Zusanli acupuncture point, and the Sanyinjiao acupuncture point at opposite side of the patient, wherein the second electrical current stimulation has a second slow-quick waveform, and the maximum current of the second electrical current stimulation is 4-15 mA.

Preferably, the step 1 and step 2 are executed synchronously.

The above-mentioned method may actually aim at the etiology in the biological and medical aspects, and results in actual therapeutic significance. In the course of treatment, the above-mentioned method is not found to have any side effects, so it can be used for a long time. The present method of the present application is non-invasive and painless, and it is acceptable for children, and suitable for family use. The method can obviously improve the symptoms of autism. The clinical manifestations is an increase of passive and active language, an improvement of social interaction-ability, emotion becoming stable, a better sleep (sleep quickly, a long time). In addition, the method is simple and do not need an acupuncturist.

Preferably, the first slow-quick waveform may have a low frequency of 0.5 Hz-10 Hz, and a high frequency of 10 Hz-20 Hz; the second slow-quick waveform has a low frequency of 0.5 Hz-10 Hz, and a high frequency of 10 Hz-20 Hz.

Preferably, the first slow-quick waveform has a low frequency of 2 Hz, and a high frequency of 15 Hz; the second slow-quick waveform has a low frequency of 2 Hz, and a high frequency of 15 Hz.

Preferably, the alternation time period of the low frequency and the high frequency of the first slow-quick waveform is 2-10 seconds; the alternation time period of the low frequency and the high frequency of the second slow-quick waveform is 2-10 seconds.

Preferably, the alternation time period of the low frequency and the high frequency of the first slow-quick waveform is 3 seconds; the alternation time period of the low frequency and the high frequency of the second slow-quick waveform is 3 seconds.

Preferably, the first electrical current stimulation and the second electrical current stimulation are separately transcutaneous acupoint electrical stimulation and/or electroacupuncture stimulation.

Preferably, the step 1 and the step 2 are applied one day at a time, a course of treatment lasts for 3 months.

Preferably, at the beginning of the course of treatment, the first electrical current stimulation has a maximum current of 3 mA-5 mA, and the maximum current is increased gradually, and to 8 mA-10 mA at the end of the course of treatment.

Preferably, at the beginning of the course of treatment, the second electrical current stimulation has a maximum current of 4 mA-6 mA, and the maximum current is increased gradually, and to 12 mA-15 mA at the end of the course of treatment.

Preferably, the method for treating autism further comprises a treatment step of behavior correction to the patient.

DETAILED DESCRIPTION OF THE INVENTION

Acupuncture originated in ancient China approximately 4000 years ago. It is based upon metaphysical concepts of "ch'i" (Qi), a supposed body energy that runs through hypothesized channels called "meridians." On these "meridians" are 365 designated acupuncture points that can be used for stimulation to balance "yin and yang" by relieving blockages in the flow of "ch'i." The physiological and anatomical basis of acupuncture points has been investigated. Acupuncture points have been found to be located in the vicinity of the small or large peripheral nerves and their bifurcations, motor points of neuromuscular attachments, blood vessels, ligaments and suture lines of the skull. A double-blind, placebo-controlled randomized study reported that true acupuncture points have higher local temperature and lower electrical resistance, compared to non-acupuncture points.

It has been found that stimulation to acupoints itself or the structure near the selected acupoints (acupuncture point), can cause synthesis and release of natural molecules. These natural molecules can directly effect on a variety of regulating system, or leading to other molecular regulation through biological pathways. These other molecules stimulate the body itself, so as to improve the physical and emotional health.

The present invention mainly relates to the following four acupuncture points: the Hegu acupuncture point, the Nei guan acupuncture point, the Zusanli acupuncture point, and the Sanyinjiao acupuncture point. As the four acupuncture points are conventional concepts in traditional Chinese medical science, no interpretation is made for the four acupuncture points. For example, it is known that the location of the Zusanli acupuncture point is defined as following: taking the left leg for sample, a person sitting on a chair, pressing the center of the kneecap with his right hand, the middle finger of his right hand extending along the shin bone, then drawing a horizontal line at the end of the middle finger, the horizontal line will cross the extension line of the index finger at a cross point, and the cross point is the position of the Zusanli acupuncture point.

The method for treating autism according to one embodiment of the present application comprising the following steps: step 1, a first electrical current stimulation of 30 minutes is applied in the vicinity of the Hegu acupuncture point and the Nei guan acupuncture point at one side of the patient, wherein the first electrical current stimulation has a first slow-quick waveform, and the maximum current of the first electrical current stimulation is 3-10 mA; and step 2, a second electrical current stimulation of 30 minutes is applied in the vicinity of the Zusanli acupuncture point, and the Sanyinjiao acupuncture point at opposite side of the patient, wherein the second electrical current stimulation has a second slow-quick waveform, and the maximum current of the second electrical current stimulation is 4-15 mA.

Figure 1:
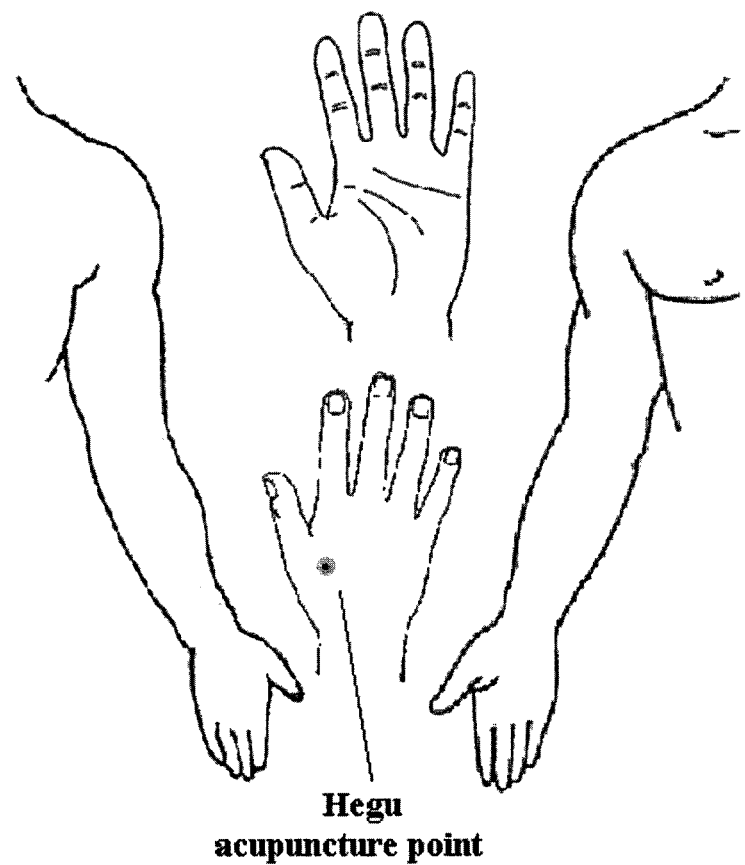
FIG. 1 is a view schematically showing the location of the Hegu acupuncture point.
Figure 2:
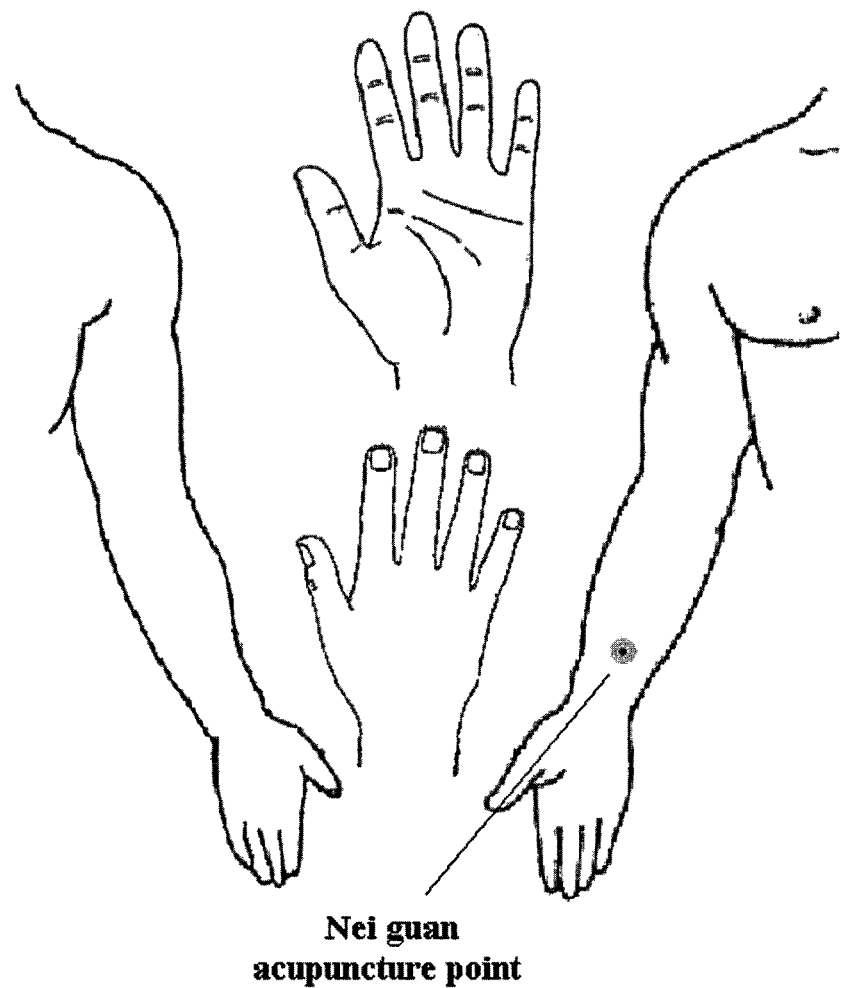
FIG. 2 is a view schematically showing the location of the Nei guan acupuncture point.
Figure 3:
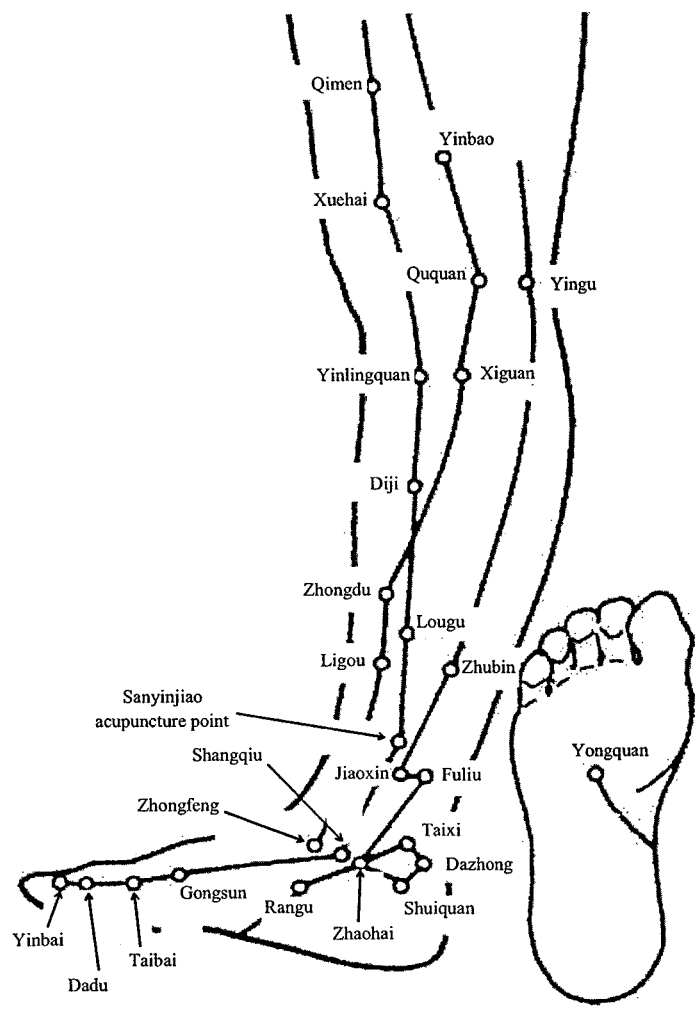
FIG. 3 is a view schematically showing the location of the Sanyinjiao acupuncture point.
Figure 4:
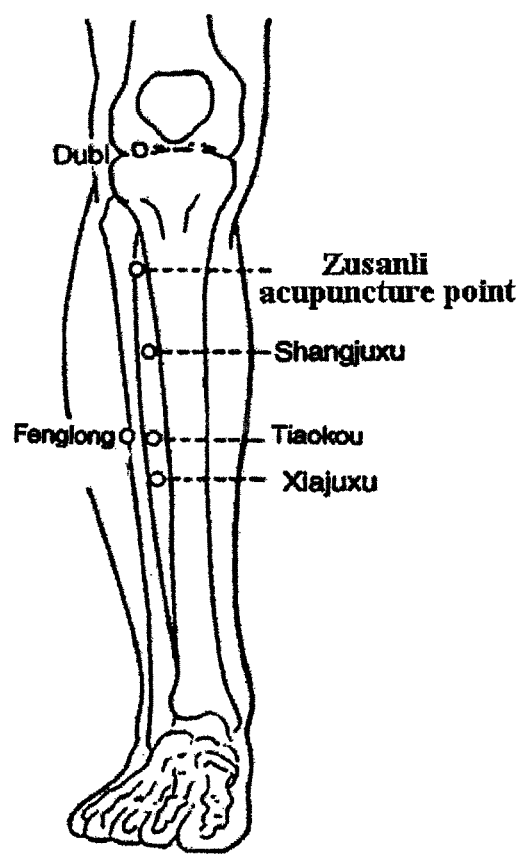
FIG. 4 is a view schematically showing the location of the Zusanli acupuncture point.
Figure 5:
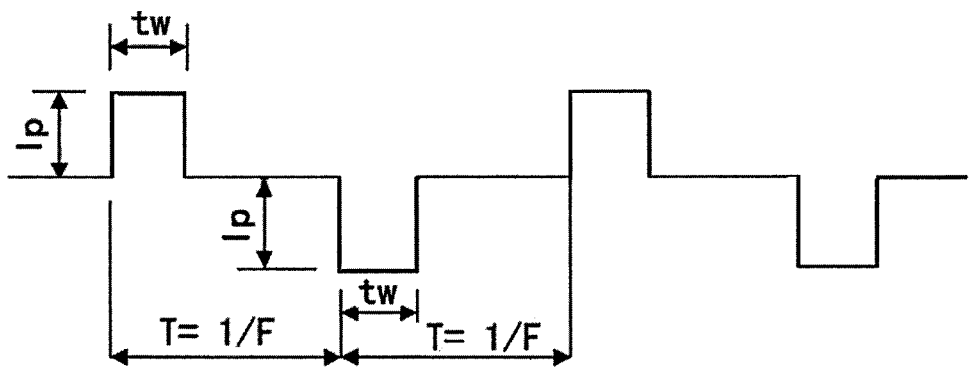
FIG. 5 is a view schematically showing the wave shape of the electrical current stimulation according to one embodiment of the present invention.

Here below is a simple description to the frequency of the stimulation (voltage or current) on the basis of FIG. 5. The current or voltage frequency referred to in this paper is a frequency for applying repetitive waveform. For example, in FIG. 5, current or voltage is a two-way alternating pulse waveform. T is a period of the pulse waveform, F is a frequency of the pulse waveform, tw is the pulse width, Ip is the pulse peak current. Although the pulse waveform shown in the figure is a two-way alternating waveform, a one-way pulse waveform (FIG. 6) is also usable.

A slow-quick wave in the article refers to a waveform including alternating low frequency waveforms (e.g. low frequency pulse) and high frequency waveform (such as high frequency pulse waveform). The frequency of the low frequency waveform is lower than the frequency of high frequency waveform.

The low frequencies of the first slow-quick wave and second slow-quick wave waveform can be selected from a range of 0.5-10 Hz independently, the high frequencies of the first slow-quick wave and the second slow-quick wave can be selected from a range of 10-20 Hz independently. In a preferred embodiment, the low frequency of the first selected from a range of wave is 2 Hz, its high frequency is 15 Hz; and the low frequency and high frequency of the second selected from a range of waves are 2 Hz and 15 Hz, respectively.

Figure 6:
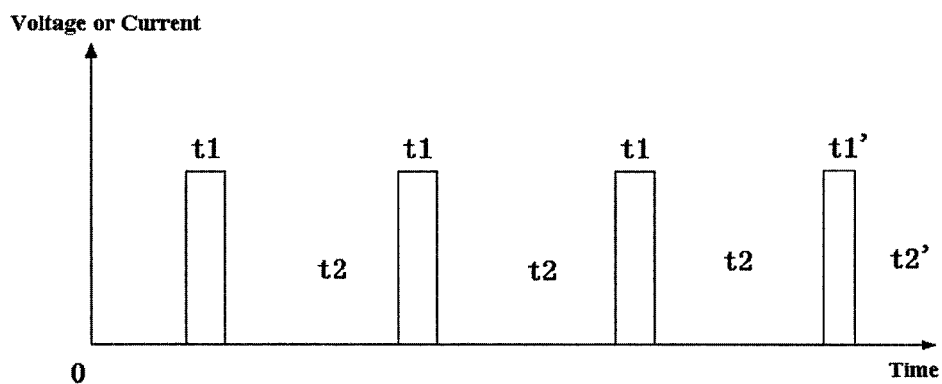
FIG. 6 is view schematically showing the wave shape of the electrical current stimulation according to another embodiment of the present invention.
Figure 7:
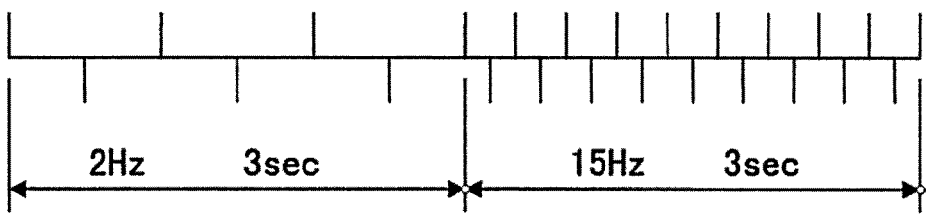
FIG. 7 is view schematically showing the wave shape of the slow-quick waveform according to an embodiment of the present invention.

The alternate time of low frequency and high frequency of the first slow-quick wave waveform is selected from a range of 2-10 seconds; and the alternate time of low frequency and high frequency of the second slow-quick wave waveform is also selected from a range of 2-10 seconds. Preferably, the alternate time of low frequency and high frequency of the first slow-quick wave waveform is 3 seconds, and the alternate time of low frequency and high frequency of the second slow-quick wave waveform is also 3 seconds. As shown in FIG. 7, the alternate time of low frequency and high frequency of the shown slow-quick wave is 3 seconds, the low frequency is 2 Hz, and the high frequency is 15 Hz. That is to say, the low-frequency waveform lasts for 3 seconds, repeated 6 times, including 6 current peaks and 6 current troughs. Then turning for high frequency operation, the high frequency waveform lasts for 3 seconds. In the 3 seconds, the high frequency waveform was repeated 45 times, with 45 current peaks and 45 current troughs. It should be pointed out that, for the sake of clarity, high frequency waveform component is shown in FIG. 6 only schematically illustrates 18 pulses, rather than 45 pulses.

In one embodiment, within each wave period (500 ms) of the low frequency waveform, the energized time (peak time, t1, corresponding to the pulse width tw under the condition of pulse waveform) is set to 0.6 ms, the trough time t2=499.4 ms.

Within each wave period (66.67 ms) of the high frequency waveform, the energized time t1' is set to 0.4 ms, the trough time t2' is set to 499.6 ms. If the high frequency is 100 Hz, the energized time is set to 0.2 ms. That is to say, the relationship between the energized time and the frequency may be a logarithmic relationship.

It is possible to select a stimulation intensity within a certain range (the current value of the first and second current stimulation) to get a desired result. We assume that the current value of the first and second current stimulation have a lowest limit of about 1 mA, or equal or greater than the individual threshold. In addition, we assume that the current value of the first and second current stimulation has a highest limit of the range is 3 times of the individual threshold, or being 24 mA. The current strength of 24 mA is usually the highest limit, because a higher current may cause muscle twitch convulsion or very uncomfortable sense. In a preferred embodiment of the invention, the intensity of the stimulation is about 2 to 3 times of the individual threshold. It should be pointed out that, because of the difference (current sensitivity) between the individuals, the actual stimulation intensity would depends on pain threshold of each individual. Although the preferred range is about 4 mA to about 16 mA, it is possible to select or adjust preferred range of stimulus intensities for each individual. For example, due to pain sensitivity decreased with age, it may need to adjust optimum range of older individuals to higher range.

Due to differences in the pain thresholds, it is usually needed to test and determine the current stimulation threshold for patients. Usually, a current with a very low strength (for example, less than 1 mA) is selected, then the strength of the current is increased slowly, until the individual notices for the first time to the current stimulation. The value of the current when the individual first notices the current stimulation, is the individual threshold for him or her.

Using transcutaneous electrical current acupoint stimulation mode, selecting Hegu and Neiguan acupoints of the upper limb (arm) of one side (such as the left side), Zusanli Sanyinjiao acupoints of the lower limb (leg) of the other side (such as the right side)contralateral (for example the right lower limb)—four points are selected; select the 2/15 Hz slow-quick wave, at the beginning stage, the strength of the current is 4 mA (for upper limb)/5 mA (for leg), according to the degree of acceptance, increasing the strength to 10 mA (for upper limb)/-15 mA (for lower limb). The above treatment is applied one time per day, a course of treatment lasts for 3 months.

In the course of treatment, the treatment side may be changed. For example, on the first day, the stimulation is applied to the corresponding points of the left upper limb and the right lower limb of the patient, and the current stimulation is applied to the corresponding points of the right upper limb and the left lower limb on the next day.

The current stimulation is applied by the following ways: first, a sheet electrode is arranged at the corresponding point of the surface of the skin, and then, the electrode is connected to an appropriate voltage.

The two acupoints of the arm and two acupoints of the leg are stimulated by a low frequency pulse therapeutic instrument. The instrument has at least two outputs. One output is connected to "Hegu" and "Neiguan" acupoints of the arm, and the other output is connected to "Sanyinjiao" and "Zusanli" acupoints of the leg. Each output constitutes of an independent loop. Current stimulation is applied through the sheet electrodes.

The therapy pulse is a two-way alternating pulse waveform. The two outputs of the low frequency pulse therapeutic instrument are synchronous in time, so as to ensure the pulse frequencies and widths are same to each other. A slow-quick wave of 2/15 Hz is applied to children. The pulse width (tw) of 2 Hz wave is 600 microseconds, the pulse width (tw) of 15 Hz wave is 400 microseconds. The 2 Hz wave and the 15 Hz wave alternates, the duration of each frequency (or period) is 3 seconds.

The treatment is made once every day, and the treatment lasts for a period of 3 months (one course). In the initial of the course, the current stimulation to the upper limb is about 3 mA to about 5 mA, and the current stimulation is gradually increased to about 8 mA to about 10 mA. In the initial of the course, the current stimulation to the lower limb is about 4 mA to about 6 mA, and the current stimulation is gradually increased to about 12 mA to about 15 mA.

Before or after the acupoint-stimulation treatment of every day, a behavior modification training of 2-3 hours is made. The core part of behavior modification treatment is task decomposition technique. The following steps is used to make behavior modification treatment.

① task decomposition.
② task training, the child is trained by only one decomposed task in a certain period of time.
③ rewarding (positive reinforcement) the achievement of the tasks, reinforce should be made for the achievement of every decomposed task, the reinforce may be food, toys and verbal or body posture recognition, the reinforce should fade gradually.
④ prompt and prompt fade, according to the development of the child, different prompt or help may be provided, with the progress of the training, the prompt or help should fade.
⑤ intertrial interval, a short break should be set between two decomposed task training.

The Experimental Data: 41 Children with Autism (Combined with Behavior Modification)

A Childhood Autism Rating Scale (CARS) is recorded by doctors or nurse according to the situation of the child with autism. An autism behavior checklist (ABC) is recorded by parents. The value of ABC scores may be divided into four intervals: 32~64, 64~77, 77~102, and 102~158. The higher the score is, it means a more severe autism behavior. The curative effect is determined according to ABC score. Obvious results: on the basis of original value, 2 or more than 2 intervals step down; Effective: on the basis of original value, one score interval step down; Invalid: on the basis of original value, no score interval step down. Tables showing the change of sleep and diet are also recorded by parents.

First group is simple behavior modification training group (n=20). Second group is acupoint electric stimulation and behavior modification training group (n=21). After a treatment course of 3 months, for the first group, the score of ABC is reduced by 19.02%, and the score of CARS is reduced by 20.29%, and the percent of obvious results is 5%. For the second group, the score of ABC is reduced by 30.94%, and the score of CARS is reduced by 34.21%, and the percent of Obvious results is 38%, showing a significant difference (P<0.001).

According to the tables showing the change of sleep, it is found that the sleep time of the child with Autism is increased by 0.5 hours, and that the time need for go to sleep is reduced by 5 minutes, by means of the acupoint electric stimulation.

If only replacing the sheet electrodes with acusectors, the method can be also effective. However, if acusectors method is selected, it is difficult to Pierce the skin of the children with the acusectors.

In a preferred embodiment of the invention, the electrode is provided with alternating current, however, the electrode may also be provided with dc.

The above is only a preferred embodiment of the invention, and is not used to limit the scope of protection of the invention.

The invention claimed is:

1. A method of treating autism comprising administering to a subject in need thereof a treatment comprising:
    step 1, applying a first electrical current stimulation of 30 minutes to the subject in the vicinity of the Hegu acupuncture point and the Nei guan acupuncture point at one side of the patient, wherein the first electrical current stimulation has a first slow-quick waveform, and the maximum current of the first electrical current stimulation is 3-10 mA; and
    step 2, applying a second electrical current stimulation of 30 minutes to the subject in the vicinity of the Zusanli acupuncture point, and the Sanyinjiao acupuncture point at opposite side of the patient, wherein the second electrical current stimulation has a second slow-quick waveform, and the maximum current of the second electrical current stimulation is 4-15 mA, wherein the step 1 and step 2 are executed synchronously,
    wherein a slow-quick waveform is a waveform including alternating low frequency waveforms and high frequency waveforms with the frequency of the low frequency waveforms being lower than the frequency of the high frequency waveforms.

2. The method for the treatment of Autism of claim 1, wherein the first slow-quick waveform has a low frequency of 0.5 Hz-10 Hz, and a high frequency of 10 Hz-20 Hz; the second slow-quick waveform has a low frequency of 0.5 Hz-10 Hz, and a high frequency of 10 Hz-20 Hz.

3. The method for the treatment of Autism of claim 1, wherein the first slow-quick waveform has a low frequency of 2 Hz, and a high frequency of 15 Hz; the second slow-quick waveform has a low frequency of 2 Hz, and a high frequency of 15 Hz.

4. The method for the treatment of Autism of claim 1, wherein the alternation time period of the low frequency and the high frequency of the first slow-quick waveform is 2-10 seconds; the alternation time period of the low frequency and the high frequency of the second slow-quick waveform is 2-10 seconds.

5. The method for the treatment of Autism of claim 3, wherein the alternation time period of the low frequency and the high frequency of the first slow-quick waveform is 3 seconds; the alternation time period of the low frequency and the high frequency of the second slow-quick waveform is 3 seconds.

6. The method for the treatment of Autism of claim 1, wherein the first electrical current stimulation and the second electrical current stimulation are separately Transcutaneous acupoint electrical stimulation and/or Electroacupuncture stimulation.

7. The method for the treatment of Autism of claim 1, wherein the step 1 and the step 2 are applied one time per day, a course of treatment lasts for 3 months.

8. The method for the treatment of Autism of claim 7, wherein at the beginning of the course of treatment, the first electrical current stimulation has a maximum current of 3 mA-5mA, and the maximum current is increased gradually, and to 8 mA-10 mA at the end of the course of treatment.

9. The method for the treatment of Autism of claim 8, wherein at the beginning of the course of treatment, the second electrical current stimulation has a maximum current of 4 mA-6 mA, and the maximum current is increased gradually, and to 12 mA-15mA at the end of the course of treatment.

10. The method for the treatment of Autism of claim 8, further comprising a treatment step of behavior correction to the subject, the treatment step of behavior correction comprising task decomposition directed toward the subject.

11. The method of claim 10, the treatment step of behavior correction further comprising task training, rewarding, prompt and/or prompt fade, and interatrial intervals directed toward the subject.

12. The method of claim 1, wherein a score of one or more of Childhood Autism Rating Scale, Autism Behavior Checklist and time to fall asleep is reduced and/or the duration of sleep is increased for the subject after treatment.

13. The method of claim 1, wherein at least one of the first and second electrical current stimulation is a transcutaneous acupoint electrical stimulation.

14. The method of claim 1 wherein at least one of the first and second electrical current stimulation is an electroacupuncture stimulation.

* * * * *